US009226843B2

(12) United States Patent (10) Patent No.: US 9,226,843 B2
Jones et al. (45) Date of Patent: Jan. 5, 2016

(54) SYSTEMS AND METHODS FOR LIMB SUPPORT

(75) Inventors: James W. Jones, Longmont, CO (US); Nathan J. Jones, Loveland, CO (US); Jodie L. Currie, Golden, CO (US); Jeffrey L. Jensen, Evergreen, CO (US)

(73) Assignee: MedEfficiency, Inc., Wheat Ridge, CO (US)

( * ) Notice: Subject to any disclaimer, the term of this patent is extended or adjusted under 35 U.S.C. 154(b) by 445 days.

(21) Appl. No.: 13/353,163

(22) Filed: Jan. 18, 2012

(65) Prior Publication Data

US 2013/0018294 A1  Jan. 17, 2013

Related U.S. Application Data

(60) Provisional application No. 61/433,873, filed on Jan. 18, 2011.

(51) Int. Cl.
*A61F 5/01* (2006.01)
(52) U.S. Cl.
CPC ............. *A61F 5/0195* (2013.01); *A61F 5/0106* (2013.01)
(58) Field of Classification Search
USPC ............ 602/5–6, 27, 28, 29, 46, 48; 128/882, 128/892, 845; 5/651; 36/140
See application file for complete search history.

(56) References Cited

U.S. PATENT DOCUMENTS

| 2,157,912 | A | 5/1939 | Nabokin |
|---|---|---|---|
| 2,516,872 | A | 8/1950 | Hauser et al. |
| 2,582,242 | A | 1/1952 | Joseph |
| 2,668,374 | A | 2/1954 | Seigle |
| 3,307,537 | A | 3/1967 | Simon et al. |
| 3,415,243 | A | 12/1968 | Sheldon |
| 3,862,629 | A | 1/1975 | Rotta |
| 3,895,405 | A | 7/1975 | Edwards |
| 3,900,024 | A | 8/1975 | Lauber et al. |
| 3,955,565 | A | 5/1976 | Johnson, Jr. |
| 3,968,577 | A | 7/1976 | Jackson |
| 4,029,087 | A | 6/1977 | Dye et al. |

(Continued)

FOREIGN PATENT DOCUMENTS

| JP | 2005058615 | 3/2005 |
|---|---|---|
| WO | WO-90/06700 | 6/1990 |

(Continued)

OTHER PUBLICATIONS

International Preliminary Report on Patentability for PCT/US2012/021763, issued Mar. 4, 2014, 7 pages.

(Continued)

*Primary Examiner* — Ophelia A Hawthorne
(74) *Attorney, Agent, or Firm* — Morrison & Foerster LLP

(57) ABSTRACT

An orthotic device according to embodiments of the present invention includes a substantially rigid internal footbed with an external rocker bottom, two struts rigidly coupled to the footbed, a paddle coupled to each strut, each paddle having an inner surface configured to face a limb of a patient, and a strap system configured to interface with the paddles for tightening around the limb, the inner surfaces of the paddles including a plurality of protrusions configured to minimize sliding of the first and second paddles with respect to the limb or with respect to a cast applied to the limb. The orthotic device may include two or more support layers on the footbed, each layer having a support aperture larger than and at least partially overlapping the support aperture below.

14 Claims, 13 Drawing Sheets

(56) References Cited

U.S. PATENT DOCUMENTS

| | | | |
|---|---|---|---|
| 4,235,228 A | 11/1980 | Gaylord et al. | |
| 4,372,300 A | 2/1983 | Drennan et al. | |
| 4,727,865 A | 3/1988 | Hill-Byrne | |
| 4,760,651 A | 8/1988 | Pon-Tzu | |
| 4,817,590 A | 4/1989 | Stancik, Jr. | |
| 4,841,956 A | 6/1989 | Gardner et al. | |
| 4,865,020 A | 9/1989 | Bullard | |
| 4,947,834 A | 8/1990 | Kartheus et al. | |
| 4,974,583 A | 12/1990 | Freitas | |
| 4,977,891 A | 12/1990 | Grim | |
| 5,014,690 A | 5/1991 | Hepburn et al. | |
| 5,094,232 A * | 3/1992 | Harris et al. | 602/16 |
| 5,186,163 A | 2/1993 | Dye | |
| 5,197,942 A * | 3/1993 | Brady | 602/5 |
| 5,203,793 A | 4/1993 | Lyden | |
| 5,329,705 A | 7/1994 | Grim et al. | |
| 5,368,551 A | 11/1994 | Zuckerman | |
| 5,378,223 A | 1/1995 | Grim et al. | |
| 5,398,354 A * | 3/1995 | Balonick et al. | 5/728 |
| 5,399,152 A | 3/1995 | Habermeyer et al. | |
| 5,415,622 A | 5/1995 | Kelley | |
| 5,421,874 A | 6/1995 | Pearce | |
| 5,441,015 A | 8/1995 | Farley | |
| 5,464,385 A * | 11/1995 | Grim | 602/27 |
| 5,496,262 A | 3/1996 | Johnson, Jr. et al. | |
| 5,527,269 A | 6/1996 | Reithofer | |
| 5,711,760 A | 1/1998 | Ibrahim et al. | |
| 5,733,647 A | 3/1998 | Moore, III et al. | |
| 5,761,834 A * | 6/1998 | Grim et al. | 36/88 |
| 5,762,622 A | 6/1998 | Lamont | |
| 5,792,084 A | 8/1998 | Wilson et al. | |
| 5,833,639 A | 11/1998 | Nunes et al. | |
| 5,839,139 A | 11/1998 | Fink | |
| 5,891,067 A | 4/1999 | Reed | |
| 5,913,841 A * | 6/1999 | Lamont | 602/65 |
| 6,026,595 A | 2/2000 | Curry | |
| 6,179,800 B1 | 1/2001 | Torrens | |
| 6,228,044 B1 | 5/2001 | Jensen et al. | |
| 6,290,662 B1 | 9/2001 | Morris et al. | |
| 6,547,751 B1 | 4/2003 | Barberio | |
| 6,585,671 B2 | 7/2003 | Rhee | |
| 6,682,497 B2 | 1/2004 | Jensen et al. | |
| 6,974,431 B2 | 12/2005 | Jensen et al. | |
| 7,476,208 B1 * | 1/2009 | Shirley | 602/27 |
| 7,597,672 B2 * | 10/2009 | Kruijsen et al. | 602/16 |
| 7,618,388 B1 * | 11/2009 | Chan | 602/23 |
| 7,666,155 B1 | 2/2010 | Jensen et al. | |
| 7,727,173 B2 * | 6/2010 | Rooney | 602/23 |
| 7,758,529 B2 | 7/2010 | Jensen et al. | |
| 8,083,704 B2 | 12/2011 | Jensen et al. | |
| 8,430,829 B1 * | 4/2013 | Marchetti | 602/3 |
| 2002/0007136 A1 * | 1/2002 | Narula et al. | 602/46 |
| 2003/0093025 A1 | 5/2003 | Rhee | |
| 2003/0195448 A1 | 10/2003 | Jensen | |
| 2004/0015112 A1 | 1/2004 | Salutterback et al. | |
| 2004/0031169 A1 | 2/2004 | Jensen et al. | |
| 2004/0111048 A1 | 6/2004 | Jensen et al. | |
| 2004/0236258 A1 * | 11/2004 | Burns et al. | 602/13 |
| 2005/0240133 A1 | 10/2005 | Rooney | |
| 2007/0167884 A1 | 7/2007 | Mangrum et al. | |
| 2009/0163843 A1 | 6/2009 | Win | |
| 2009/0306565 A1 * | 12/2009 | Chan | 602/28 |
| 2011/0010862 A1 * | 1/2011 | Mitchell | 5/646 |
| 2011/0288458 A1 | 11/2011 | Jones et al. | |

FOREIGN PATENT DOCUMENTS

| | | |
|---|---|---|
| WO | WO-00/40202 | 7/2000 |
| WO | WO-03/029780 | 4/2003 |
| WO | WO-2006/043080 | 4/2006 |
| WO | WO-2008/021986 | 2/2008 |
| WO | WO-2011/130676 | 10/2011 |

OTHER PUBLICATIONS

International Search Report and Written Opinion for PCT/US2012/021763, mailed May 18, 2012, 8 pages.

* cited by examiner

SYSTEMS AND METHODS FOR LIMB SUPPORT

CROSS-REFERENCE TO RELATED APPLICATIONS

This application claims the benefit of U.S. Provisional Patent Application Ser. No. 61/433,873, filed on Jan. 18, 2011, which is incorporated herein by reference in its entirety for all purposes.

TECHNICAL FIELD

Embodiments of the present invention relate generally to limb orthotics, and more specifically to methods and devices for treating foot ulcerations and/or injuries to the plantar area of the foot.

BACKGROUND

Embodiments of the present invention relate generally to limb off-weighting or off-loading utilized for the treatment of ulcerations and/or injuries to the plantar area of the foot. The development of effective means for treating foot sores or ulcerations, especially diabetic foot ulcerations, presents a significant medical challenge. Diabetic foot ulcers result in numerous lower extremity amputations per year and account for more hospitalizations than any other single complication of diabetes. A large percentage of diagnosed diabetics suffer from foot ulcerations. In fact, foot ulcers are the leading cause of hospitalization of patients with diabetes and account for a significant percentage of the costs related to diabetic care.

The burdens of such complications can also have a devastating effect on patients and their families. Patients' quality of life can rapidly decline leaving them unable to work, and dependent on family members to spend their time and resources caring for the patient. The problem is compounded by the fact that many diabetics suffer from peripheral neuropathy and thus cannot feel pain. Because pain is often a primary incentive for patient compliance, neuropathy patients frequently do not comply with voluntary off-weighting or off-loading techniques, resulting in further deterioration of the wound and possibly leading to infection. Complicating matters further, the progressive disorder "Charcot Neuroarthropathy" significantly deforms the foot and the associated ulcerations, making off-weighting or off-loading measures even more difficult.

One common cycle for this medical complication is chronic foot ulceration, infection, hospitalization, amputation and rehabilitation. This costly cascade of events need not take place because two-thirds of diabetic amputees do have an adequate blood supply to heal ulcerations. One significant factor for effective treatment can often be to offload the patient's weight from the ulcerated site to give the ulcers an opportunity to heal.

While some devices have been specifically designed to address the need to treat patients suffering plantar ulcers, it should also be noted that a number of related adjustable leg casts have also been developed. Such casts, however, are often designed primarily for fracture care rather than for treating plantar ulcers. Existing devices for treating plantar ulcerations are often time-consuming to apply and/or relatively expensive, or result in sliding, movement or unintentional rearrangement of the device or its components shortly after application or during ambulation.

SUMMARY

Some embodiments of the invention address a particularly difficult diabetic complication associated with plantar ulcerations related to diabetes: Charcot Neuroarthropathy. Charcot Neuroarthropathy is a progressive condition affecting the foot and ankle characterized by joint dislocations, pathologic fractures, and debilitating deformities. The progressive destruction of bone and soft tissues at weight-bearing joints often causes significant disruption of the bony architecture. Those embodiments take into account such deformities, allow for off-loading from the deformed and ulcerative site, and ultimately address one of the most debilitating causes of amputation. It should be noted that the FDA does not even allow wounds associated with Charcot Neuroarthropathy into diabetic foot clinical trials for evaluation as they are considered too difficult to treat in terms of off-loading.

An orthotic device according to embodiments of the present invention includes a footbed with a substantially rigid internal footbed and an external rocker sole, a first strut rigidly coupled to the footbed, a second strut rigidly coupled to the footbed, a first paddle coupled to the first strut, the first paddle including a first inner surface adapted to face a limb of a patient, a second paddle coupled to the second strut, the second paddle comprising a second inner surface adapted to face the limb of the patient, and a strap system configured to interface with the first and second paddles for tightening around the limb. The first inner surface and second inner surface may include a plurality of protrusions, and the plurality of protrusions may be configured to minimize sliding of the first and second paddles with respect to the limb or with respect to a cast applied to the limb. The footbed may include a first support layer located on the footbed, the first support layer including a first aperture, and a second support layer located on the first support layer, the second support layer comprising a second aperture larger than the first aperture and at least partially overlapping the first aperture. The footbed may further include a third support layer located on the second support layer, the third support layer including a third aperture larger than the first and second apertures and at least partially overlapping the first and second apertures.

An orthotic device according to embodiments of the present invention includes a footbed with an internal footbed and an external sole, wherein the internal footbed is substantially rigid, a first strut coupled to the footbed, a second strut coupled to the footbed, a paddle coupled to the first strut, the paddle comprising an inner surface configured to face a limb of a patient, a circumferential attachment system configured to interface with the paddle for tightening around the limb, wherein the inner surface includes a mechanical interlock feature, and wherein the mechanical interlock feature is configured to minimize sliding of the paddle with respect to the limb or with respect to a cast applied to the limb and to increase an area over which forces from the first strut are transmitted to the limb or the cast applied to the limb.

The orthotic device of the previous paragraph, wherein the paddle is a first paddle, wherein the inner surface is a first inner surface, and wherein the mechanical interlock feature is a first mechanical interlock feature, the orthotic device further including a second paddle coupled to the second strut, the second paddle comprising a second inner surface configured to face the limb of the patient, wherein the second inner surface includes a second mechanical interlock feature, and wherein the second mechanical interlock feature is configured to minimize sliding of the second paddle with respect to the limb or with respect to the cast applied to the limb.

The orthotic device of any of the previous two paragraphs, further including the cast applied to the limb.

The orthotic device of any of the previousl three paragraphs, wherein the first and second mechanical interlock features are a plurality of protrusions, and wherein the plurality of protrusions is configured to minimize sliding of the first and second paddles with respect to the cast.

The orthotic device of any of the previous four paragraphs, wherein the cast comprises a plurality of indentations, and wherein at least some protrusions of the plurality of protrusions are configured to protrude within at least some indentations of the plurality of indentations when the circumferential attachment system is applied to the orthotic device.

The orthotic device of any of the previous five paragraphs, wherein an angle between the first strut and the inner surface is adjustable, the orthotic device further comprising a spring element configured to bias the inner surface away from the first strut.

The orthotic device of any of the previous six paragraphs, wherein the angle is selected to permit the paddle to accommodate calves of varying sizes.

The orthotic device of any of the previous seven paragraphs, wherein the spring element is a leaf spring coupled to the paddle and coupled to the first strut.

The orthotic device of any of the previous eight, wherein the angle is formed by an inside of a wedge-shaped pocket in the paddle.

An orthotic device according to embodiments of the present invention includes a footbed comprising an internal footbed and an external sole, wherein the internal footbed is substantially rigid, a first strut coupled to the footbed, a second strut coupled to the footbed, a paddle coupled to the first strut, the paddle comprising an inner surface configured to face a limb of a patient, a first support layer located on the footbed, the first support layer comprising a first aperture, and a second support layer located on the first support layer, the second support layer comprising a second aperture larger than the first aperture and at least partially overlapping the first aperture.

The orthotic device of any of the previous ten paragraphs, further including a third support layer located on the second support layer, the third support layer comprising a third aperture larger than the first and second apertures and at least partially overlapping the first and second apertures.

The orthotic device of any of the previous eleven paragraphs, wherein the first support layer is denser than the second support layer.

The orthotic device of any of the previous twelve paragraphs, wherein the first support layer is denser than the second support layer, and wherein the second support layer is denser than the third support layer.

The orthotic device of any of the previous thirteen paragraphs, wherein the first support layer is adhered to the second support layer.

The orthotic device of any of the previous fourteen pararagraphs, wherein the first support layer is adhered to the second support layer, and wherein the second support layer is adhered to the third support layer.

The orthotic device of any of the previous fifteen paragraphs, wherein the second aperture is at least partially enclosed by one or more of a mesh, a thinner layer, a material that is at a lower density than material out of which the second aperture is formed, and a memory foam.

The orthotic device of any of the previous sixteen paragraphs, wherein at least a portion of the second aperture is preformed in the second support layer.

The orthotic device of any of the previous seventeen paragraphs, wherein one or more other apertures are preformed in the second support layer.

The orthotic device of any of the previous eighteen paragraphs, wherein the second support layer comprises perforations or markings for other apertures or differently sized apertures in addition to the second aperture.

The orthotic device of any of the previous nineteen paragraphs, wherein the second support layer comprises perforations or markings for other apertures or differently sized apertures in addition to the second aperture.

The orthotic device of any of the previous twenty paragraphs, wherein the external sole is an external rocker sole configured to permit ambulation.

An orthotic device according to embodiments of the present invention includes a footbed comprising an internal footbed and an external rocker sole, wherein the internal footbed is substantially rigid, a first strut coupled to the footbed, a second strut coupled to the footbed, a paddle coupled to the first strut, the paddle comprising an inner surface configured to face a limb of a patient, and a foot support assembly located on the footbed, the foot support assembly molded as a single piece and comprising an aperture extending from a top to a bottom of the foot support assembly, wherein the aperture is configured to circumscribe a foot ulcer, a Charcot deformity, or a transmetatarsal amputation site, and wherein at least one dimension of the aperture decreases along a direction from the top to the bottom of the foot support assembly.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
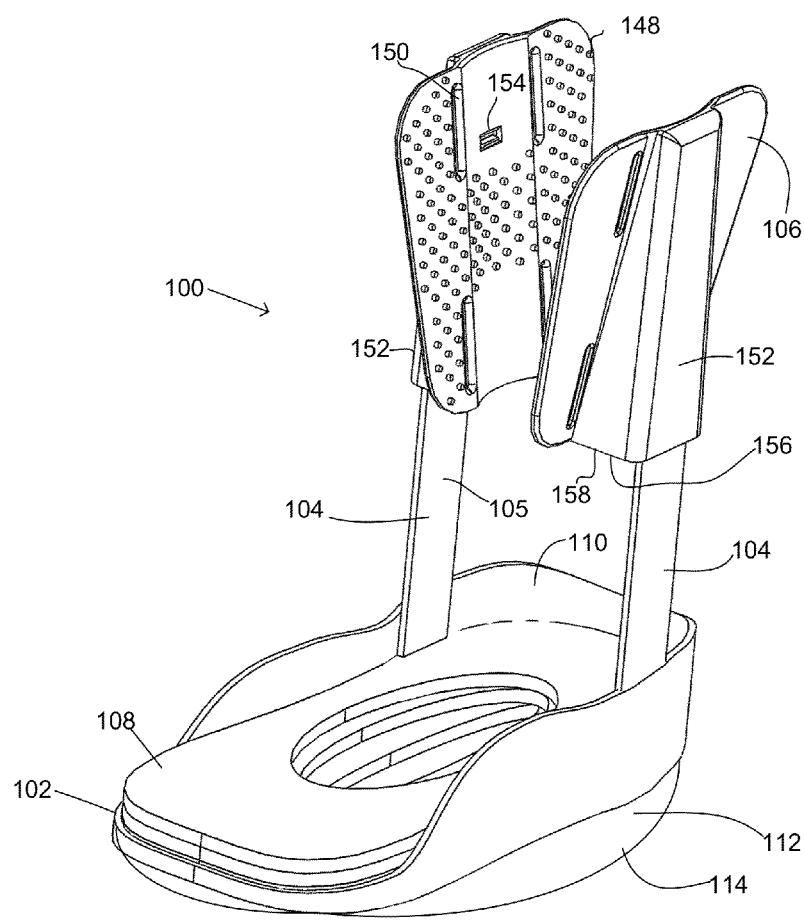
FIG. 1 illustrates a perspective view of an off-weighting boot according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
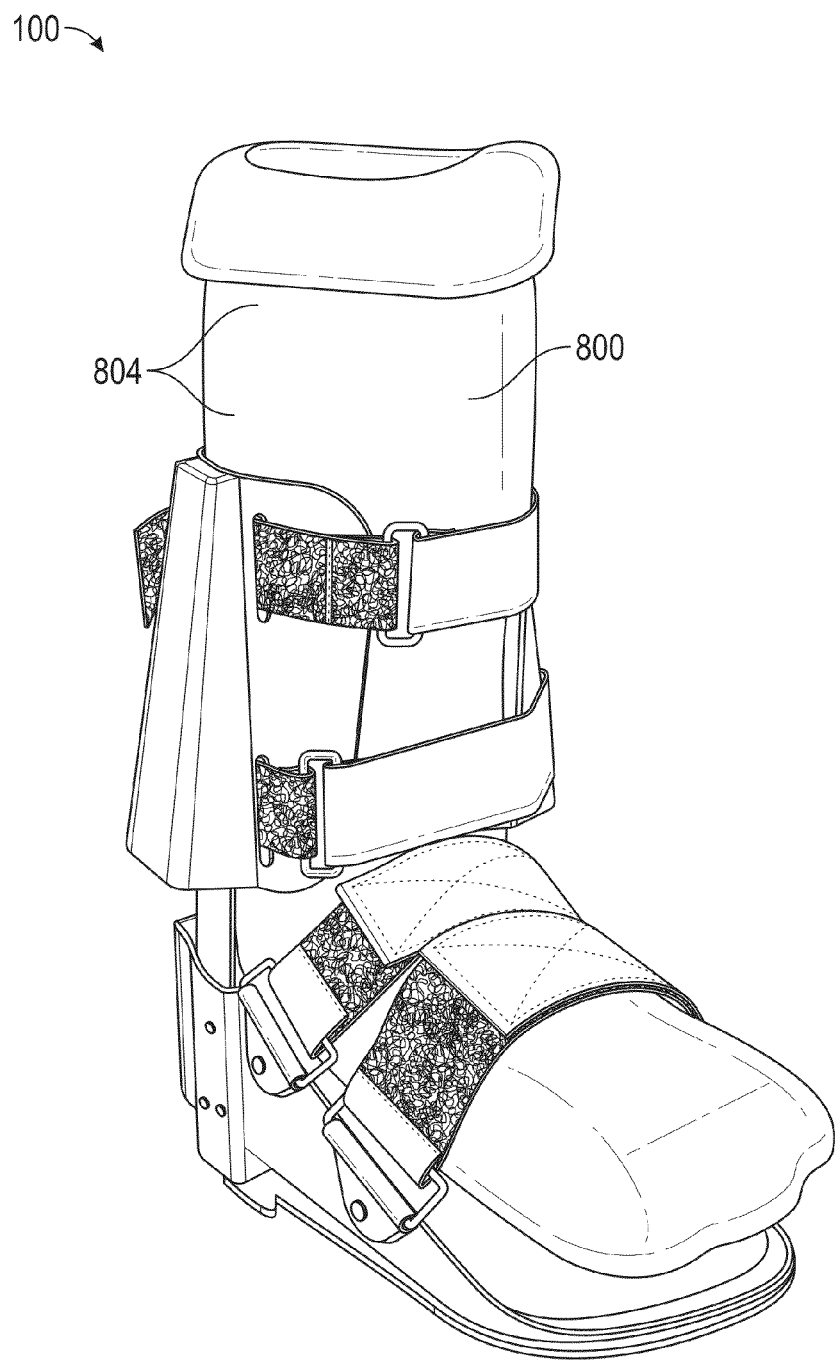
FIG. 2 illustrates a perspective view of an off-weighting boot with a hardenable cast placed therein, according to embodiments of the present invention.
Figure 3:
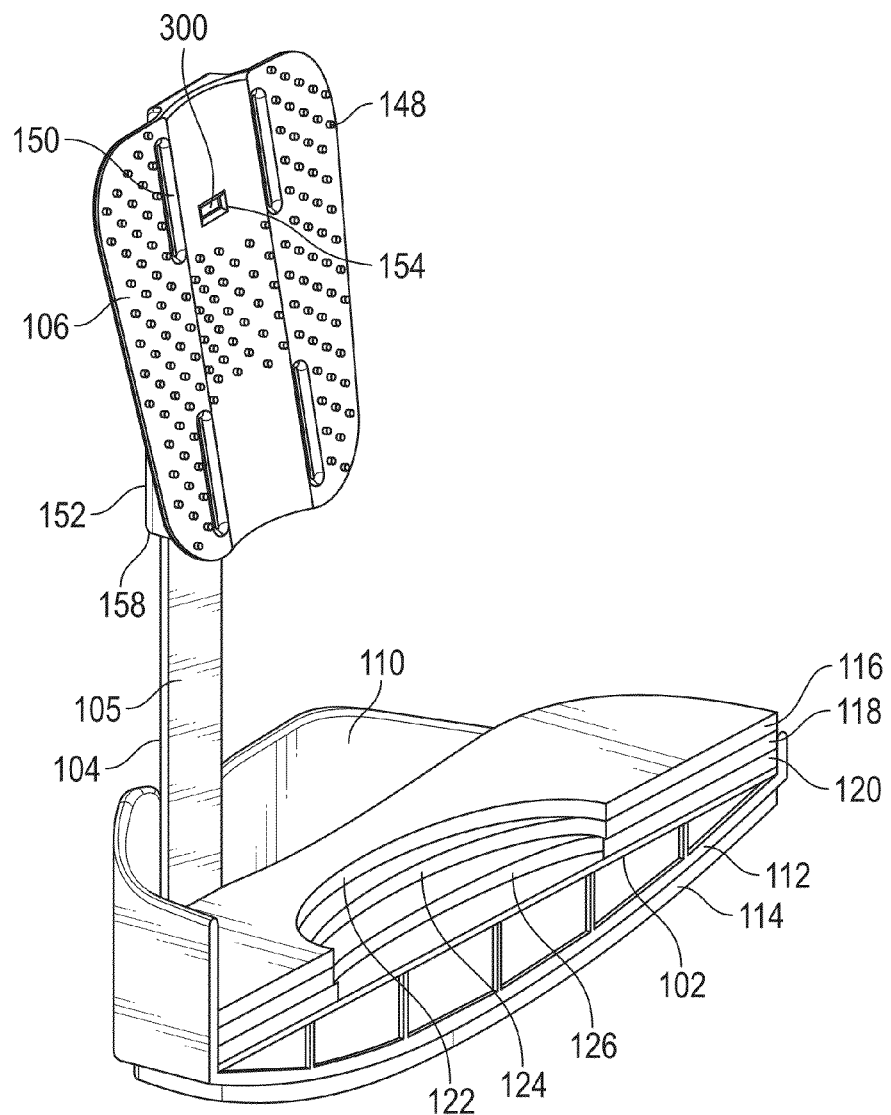
FIG. 3 illustrates a cut away perspective view of the off-weighting boot of FIG.

FIGS. 1 and 2 depict an off-weighting boot 100 according to embodiments of the present invention. FIG. 3 illustrates a cut away view of the boot in FIG. 1. In one embodiment, the boot 100 is configured to operate over, and in conjunction with, another orthopedic device such as a hardenable cast 800. In other embodiments, the boot 100 is configured to operate without a separate orthopedic device. In an embodiment, the boot 100 includes a rigid footbed 102 to which two side struts 104 are coupled. A support assembly 108 is coupled to the rigid footbed 102, and the side struts 104 are coupled to paddles 106. As used herein, the term "coupled" is used in its broadest sense to refer to elements which are connected, attached, and/or engaged, either directly or integrally or indirectly via other elements, and either permanently, temporarily, or removably.

As illustrated in FIGS. 1-3, the outer boot 100 includes a substantially vertical sidewall portion 110 attached to the rigid footbed 102. The sidewall portion 110 may have foam or rubber padding along its inner surface. In some embodiments, the rigid footbed is coupled to a curved rocker sole 112 with a tread 114 of rubber or the like. The curved rocker sole 112 is configured to increase stability and facilitate off-loading of the patient's foot, according to embodiments of the present invention.

Figure 4:
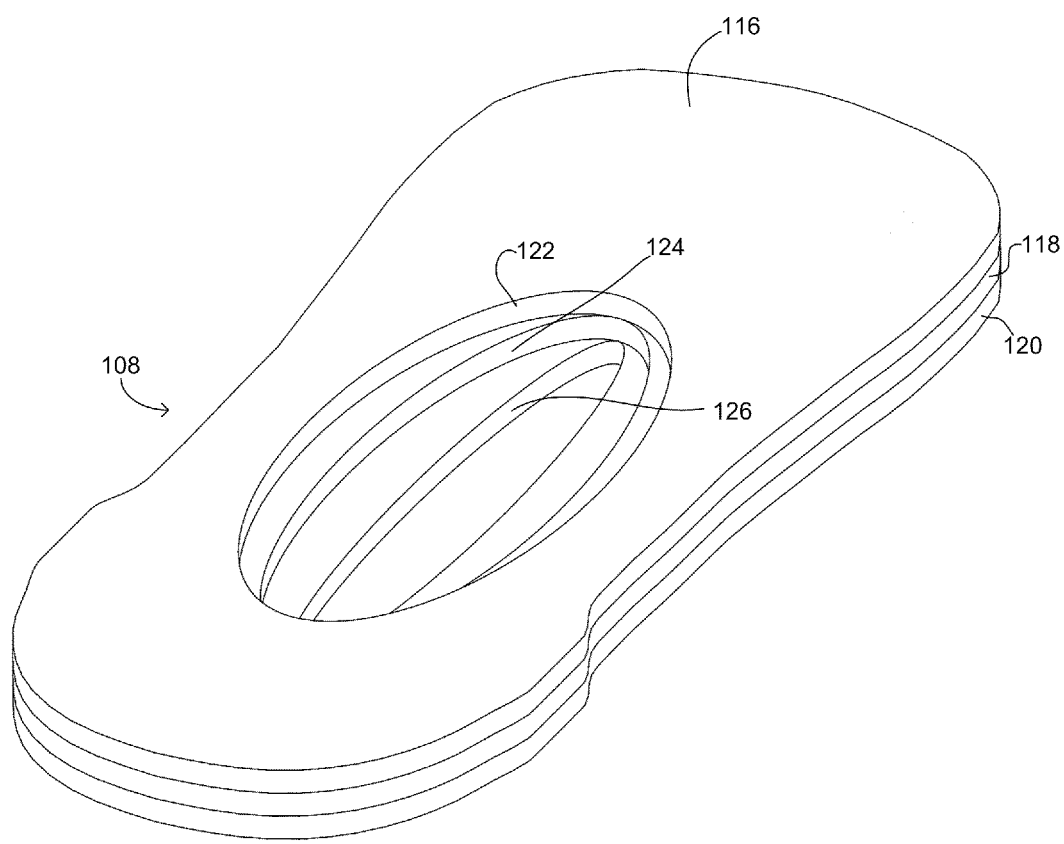
FIG. 4 illustrates a perspective view of a multi-layer foot support assembly according to embodiments of the present invention.
Figure 5:
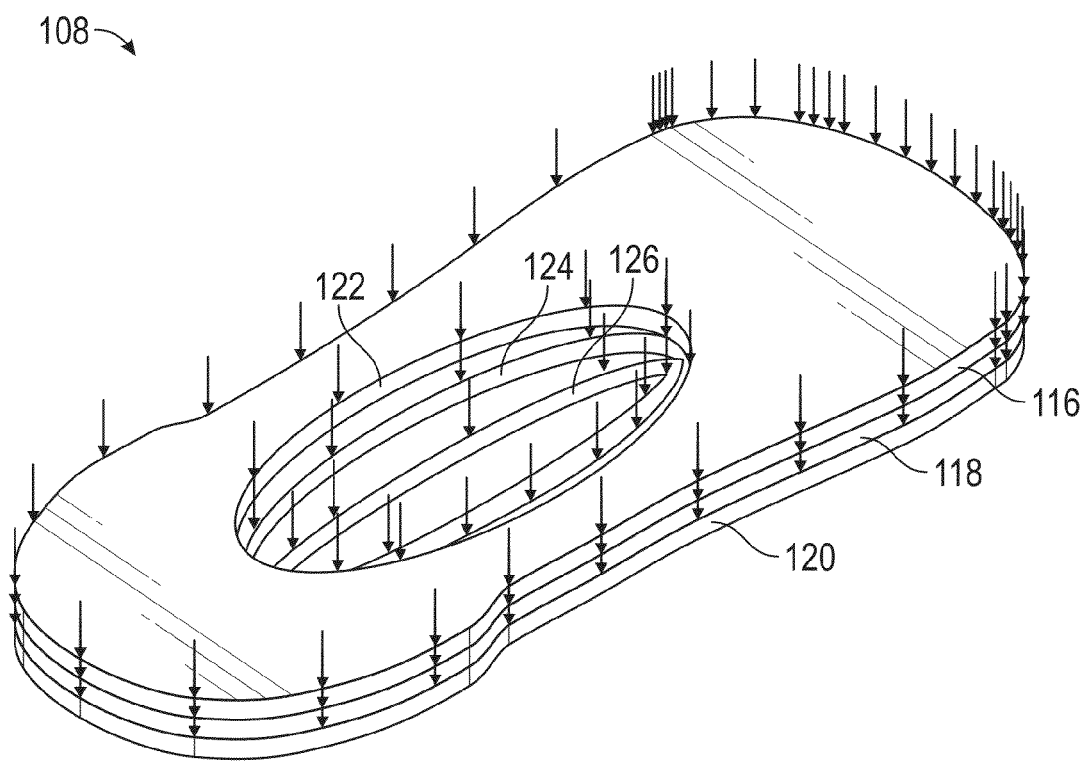
FIG. 5 illustrates a perspective view of a multi-layer foot support assembly of according to embodiments of the present invention.

The support assembly 108 may include multiple layers of support material; in one embodiment illustrated in FIGS. 4 and 5, the support assembly 108 includes an upper support layer 116, a middle support layer 118, and a lower support layer 120. In other embodiments, the support assembly 108 has only one support layer. In yet other embodiments, each support layer is formed from a supportive material, such as foam or rubber. In other embodiments, the composition of support layers 116, 118, 120 varies from layer to layer to take advantage of various properties of different materials. For example, upper support layer 116 can comprise a soft or less dense material, which provides comfort but a lower degree of support, while middle support layer 118 and lower support layer 120 may comprise a more firm or dense material, which supplies a higher degree of support. Various foams (open cell or closed cell foams), silicones (compressible or non-compressible), polyurethanes, and/or gels may be used to provide the sequence of firmness or durometer. In some embodiments, the lower support layer is formed of an EVA-based material having a hardness of 35-55 Shore A. The middle layer is also formed of an EVA-based material with a hardness of 20-40 Shore A. The top layer is formed of a closed cell EVA-based material with a hardness of 20-25 Shore A, such as P-Cell® manufactured by Acor®. The support layers 116, 118, and 120 may be fused or otherwise attached together to facilitate easy application. The support assembly 108 may also be molded of a single piece of foam material, according to embodiments of the present invention. Such a single piece molded support assembly 108 may include one or more apertures which narrow or decrease in size from top to bottom, according to embodiments of the present invention. Such a single piece molded support assembly 108 may include one kind of material, and/or may include two or more kinds or layers of materials which are co-molded, for example.

As illustrated in FIG. 3, the apertures 122, 124, 126 form what may be referred to as a "well" which receives a Charcot deformity or foot ulceration. A cushioning element, such as, for example, a gel-filled packet or an air-filled packet, may be placed within or under this well, to provide additional comfort to the user, and to minimize hard surface contact.

In FIGS. 4 and 5, support layers 116, 118, and 120 each include a support aperture 122, 124, and 126, respectively. In other embodiments, each support layer may have more than one support aperture or may have no support apertures. In one embodiment, the support apertures are configured to circumscribe a foot sore or ulceration on the bottom of a patient's foot, so as to protect the foot sore from contact with the support assembly 108 or rigid footbed 102. The support apertures also protect the foot sore from pressure asserted during ambulatory activities, according to embodiments of the present invention. In cases in which the patient has more than one foot sore, the support layers may include multiple support apertures, with each aperture configured to circumscribe a single foot sore. Alternatively, the support layers may comprise support apertures configured to protect multiple foot sores. The footbed 102 and support layers 116, 118, 120 accommodate a Charcot deformity to ensure that no additional trauma is imparted to the injury during use of the boot 100, according to embodiments of the present invention. These one or more support layers essentially encase the Charcot protrusion in hardened and/or semi-hardened forms to protect the deformity from "bottoming out" on the rigid footbed 102, according to embodiments of the present invention. As such, the boot 100 may be referred to as a "floating-type" device, which hinders "bottoming out" even for heavier patients. The support layers and support apertures may also be configured to address other orthopedic or medical issues, such as bunions, plantar fasciitis, heel spurs, stress fractures, fallen arches, and the like, according to embodiments of the present invention.

In one embodiment, the support layers 116, 118, and 120 have support apertures that vary in size to add increased support while establishing a protective cavity around the foot sore. Specifically, the support layer closest to the foot, for example upper support layer 116 in FIGS. 4 and 5, includes an aperture 122 configured to circumscribe a particular foot sore or a particular area of the foot. The next support layer, for example the middle support layer 118 in FIGS. 4 and 5, includes a support aperture 124 that is smaller in size than support aperture 122, which enables the middle support layer to help bear ambulatory pressure without putting pressure on the cast in the vicinity of the foot sore. The next support layer, for example the lower support layer 120, has a support aperture 126 smaller than support aperture 124, which permits the lower support layer to further bear ambulatory pressure without putting pressure on the cast in the vicinity of the foot sore. This minimizes both ground reactive forces and shearing stress in this area. The arrows shown in FIG. 5 demonstrate that the pressure placed each layer decreases from layer 116 to layer 120. In fact, plantar pressure at the end of the lowest aperture 126 may be negligible. While in FIG. 5 arrows are only shown on the perimeter of the layers for clarity, in practice the pressure will be across the surface of the support layers as well. In other embodiments, more or less than three support layers can be used to form the cavity, with each support layer having support apertures of decreasing size from top to bottom. The shape of each support aperture can vary to accommodate particular patient needs. In one embodiment, each support layer has support apertures with a substantially identical shape and size.

In those embodiments in which a support layer has multiple support apertures, for example upper support layer 116, the support apertures on the remaining support layers can be configured to match the configuration of the support apertures on the upper support layer. In one embodiment, the remaining support layers can have support apertures of decreasing size, relative to the support aperture located above them. The support assembly 108 may also utilize a support layer without any support apertures; that support layer is placed below at least one support layer having a support aperture so that the foot sore is not aggravated during ambulatory activity, according to embodiments of the present invention. In addition, the support apertures in the support layers can be configured to accommodate extra padding over the foot sore or can be configured to circumscribe a wound access window in an orthopedic device, such as a proximal flange in a foot cast. Thus, the support assembly 108 can comprise one or many support layers, according to particular patient needs, and each support layer may include none or several support apertures tailored to address specific medical issues.

The support assembly 108 may include support apertures 122, 124, 126 which are formed by removing a portion of each respective layer 116, 118, 120, according to embodiments of the present invention. For example, each layer may include one or more preformed or perforated support aperture locations as removable pieces, which permit the medical professional to decide at or during the time of treatment where to create the apertures. For example, the preformed or perforated support aperture locations may correspond to the apertures 122, 124, 126 shown in FIG. 5. Other support assembly 108 systems may be used, for example a support assembly 108 that has support apertures corresponding to a transmetatarsal amputation (TMA) wound or foot deformity on a patient's foot. Also, although support apertures 122, 124, 126 are described as holes, support apertures may also or instead be zones where the layer material or the support assembly 108 material is thinner, is of a lower density, is formed of more conforming foam, and/or includes a mesh portion. For example, the apertures 124 and 126 may be holes, but aperture 122 may include a thin mesh layer covering the opening, such that aperture 122 is not a hole per se, but rather an area that is thinner than the surrounding material, and which thus does not apply significant pressure to the area bounded by the aperture 122, according to embodiments of the present invention.

According to embodiments of the present invention, the one or more support apertures 122, 124, 126 are formed in the shapes of ovals, with the longest dimension of the ovals extending longitudinally from the front to the back of the footbed 102. According to some embodiments of the present invention, each of the support layers 116, 118, 120 have an outer shape that substantially corresponds to an inner shape of the footbed 102 and/or side wall 110. The support apertures 122, 124, 126 may each be ovals with the same longest dimension, and differing lateral dimensions (the lateral dimensions extending in a direction between medial and lateral sides of the footbed 102). For example, the support assembly 108 includes three layers 116, 118, 120 with each layer having a support aperture 122, 124, 126, respectively, with the support apertures 122, 124, 126 formed in the shape of ovals with their longest dimension aligned longitudinally from the front to back of the footbed 102, their longest dimensions being substantially the same, with the lowermost layer 120 having an aperture 126 with the smallest lateral dimension, the middle layer 118 having an aperture 124 with a lateral dimension larger than the lateral dimension of the aperture 126, and the top layer 116 having an aperture 122 with a lateral dimension larger than the lateral dimension of the apertures 126 and 124, according to embodiments of the present invention. According to embodiments of the present invention, the rocker sole 112, in combination with the one or more layers 116, 118, 120, creates a concavity below the patient's foot to protect, and minimize irritation of, a plantar ulceration. The top surface of the footbed is flat and will allow for accommodation of any deformities, according to embodiments of the present invention.

As shown in FIGS. 1-3, the side struts 104 may be riveted to the footbed 102 or to the sidewall portion 110; alternatively, the side struts 104 may be formed integrally with the footbed 102 or the sidewall portion 110. At their other end, the side struts 104 may each be riveted to or otherwise coupled inside of a wedge-shaped cavity 556 in the strut connector 152 of the paddle 106 (see FIG. 7), according to embodiments of the present invention. The side strut 104 is rigidly coupled to both the paddle 106 and the footbed 102, such that a downward force imparted onto the paddle 106 is transmitted through the side strut 104 and into the footbed, according to embodiments of the present invention. In one embodiment, the side struts 104 are placed so that the inner surface 105 of the side struts 104 substantially parallels a patient's tibia and fibula. According to some embodiments of the present invention, the side struts 104 are rigidly coupled to the footbed 102 in a manner which is removable or reversible, so as to permit the side struts 104 to be removed from the footbed 102 or folded with respect to the footbed 102, according to embodiments of the present invention. The side struts 104 may be removable easily (e.g. with the push of a button or release of a clasp), or may require the use of tools to be removable, according to embodiments of the present invention. The side struts 104 may also be configured to pivot with respect to the footbed 102, according to embodiments of the present invention. This releasable and/or pivoting attachment permits a rigid attachment to the footbed 102 when in the use configuration, with such rigid attachment permitting virtually no movement of the strut 104 with respect to the footbed 102, according to embodiments of the present invention. As such, a strut 104 may be rigidly coupled with the footbed 102 by not permitting relative movement during use, even if such coupling is also pivotable and/or removable.

Figure 6:
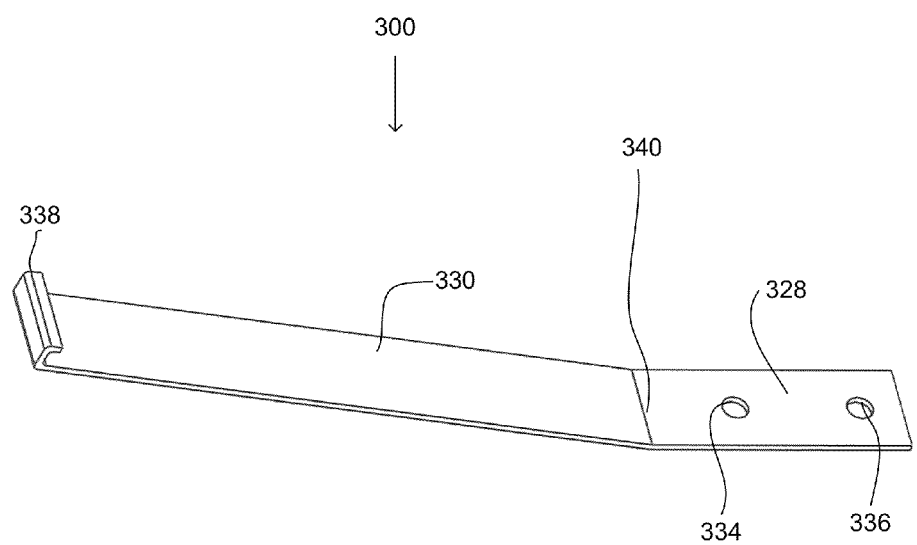
FIG. 6 illustrates a perspective view of a spring element, according to embodiments of the present invention.

FIG. 6 illustrates a spring element 300, according to embodiments of the present invention. Spring element 300 includes a strut attachment portion 328 and a paddle attachment portion 330. The strut attachment portion 328 may include one or more apertures 334, 336 for receiving a screw, rivet, nail, bolt, or other attachment device in order to couple the spring element 300 with a strut 104, according to embodiments of the present invention. Paddle attachment portion 330 may include a hook element 338 configured to hook onto an aperture in the paddle 106, according to embodiments of the present invention. The hook element 338 may be formed by bending the spring element 300, according to embodiments of the present invention. The spring element 300 may be formed of a strong yet resilient material, according to embodiments of the present invention.

Figure 7:
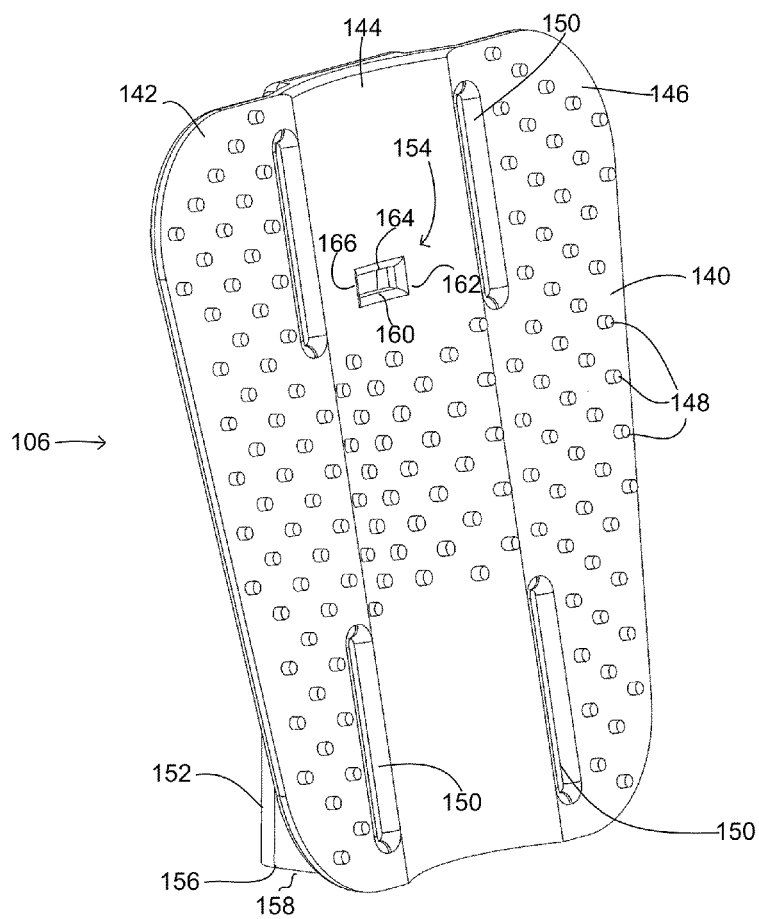
FIG. 7 illustrates a paddle according to embodiments of the present invention.

FIG. 7 illustrates a paddle 106 with an inner side 140, according to an embodiment of the present invention. The paddle 106 includes three paddle sections 142, 144, and 146. Each paddle section may be curved to conform to a portion of a patient's body or orthopedic device. Each paddle section may be formed separately and joined together in such a manner that the paddle 106 is curved to conform to a portion of a patient's leg or orthopedic device. Alternatively, the paddle sections 142, 144, and 146 may be formed integrally with each other. The paddles 106 may be formed in varying sizes and/or shapes, and may be formed of a thermoplastic elastomer or thermoplastic rubber or thermoplastic vulcanizate, such as Santoprene™, to promote a desirable balance of flexibility, strength, and durability, according to embodiments of the present invention. The inner side 140 also includes one or more protrusions 148, according to embodiments of the present invention. The protrusions 148 are cylindrically shaped; other shapes, for example cones, hemispheres, or rectangular prisms, could be used instead of, or in combination with, cylindrical protrusions 148. In addition, the protrusions 148 can be arranged in various patterns, only one of which is shown as an example in FIG. 7. The protrusions 148 may be arranged and configured to engage an orthopedic device, such as a cast, so that the boot 100 is more firmly secured to the orthopedic device. In addition, the protrusions 148 can act to transfer forces from the boot 100 to the orthopedic device, which further enhances the transfer of forces through the boot 100 instead of through the patient's leg, thereby further protecting the patient, according to embodiments of the present invention. In some embodiments the paddle 106 and/or the protrusions 148 are formed of rubber or of a similar material. The paddle may include more or fewer protrusions 148 than shown, and the protrusions 148 may be smaller and/or larger than those shown, according to embodiments of the present invention.

The protrusions 148 are one type of mechanical cast interlocking feature which may be included on the paddles 106, according to embodiments of the present invention. Other mechanical cast interlocking features may be included on the paddles 106 and/or the cast 800, to permit a mechanical interlock between at least part of the paddle 106 and at least part of the cast 800, according to embodiments of the present invention. For example, one or a combination of waves, ridges, protrusions, indentations, barbs, tines, hooks, spikes, grit, and/or surface texture may be applied to the paddle 106 and/or cast 800 in order to improve the mechanical interlock (e.g. the resistance to sliding or disengagement) between the paddle 106 and the cast 800, according to embodiments of the present invention. The mechanical cast interlocking feature or features adhere the paddles 106 to the cast while improving distribution of the load over a larger area at the cast-paddle interface, according to embodiments of the present invention.

Figure 8:
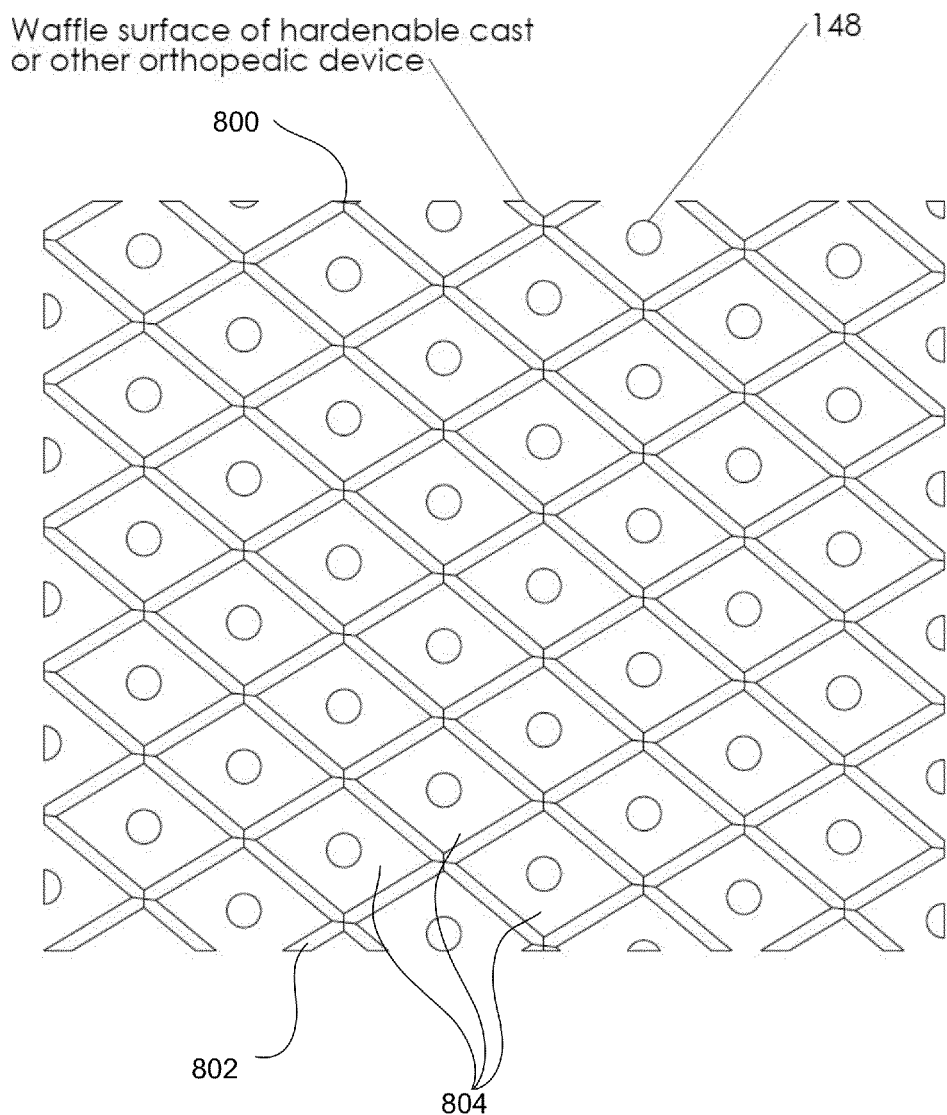
FIG. 8 illustrates cut away side view of a paddle and a hardenable cast according to embodiments of the present invention.

The underlying orthopedic device may be one or more orthopedic devices, for example a water-hardenable cast, as shown and/or described in U.S. Pat. No. 7,758,529, issued on Jul. 20, 2010, which is incorporated by reference herein for all purposes. For example, such hardenable casts may include a textured outer surface, for example an outer surface having repeating patterns of indentations. In such cases, the size and/or arrangement of the protrusions 148, which may also be referred to as nubs, may correspond with the size and/or arrangement of indentations on the outer surface of the hardenable cast. The hardenable cast may first be applied to a patient and permitted to harden or to substantially harden, and then the boot 100 may be secured to the patient's limb over the cast, according to embodiments of the present invention. For example, in FIG. 8 a portion of a hardenable cast 800 is shown. FIG. 2 also illustrates a hardenable cast 800 inserted into boot 100, according to embodiments of the present invention. The cast has a waffle surface 802. The protrusions 148 are configured to secure the boot to the cast by contacting the cast within multiple waffle recessions 804. According to embodiments of the present invention, the paddles 106 include ten protrusions 148 per square inch, which may also correspond to the density of waffle recessions 804 on the hardenable cast 800. According to other embodiments of the present invention, the density of protrusions 148 does not correspond with the density of recessions 804, but the protrusions 148 otherwise interface with, fit within, and/or mate engagingly with the recessions 804 so as to discourage the paddle 106 from slipping or sliding relative to the cast 800. Although a hardenable cast with a textured and/or waffle surface is shown in FIG. 2, the boot 100 may also be used with other kinds of casts, including hardenable casts, and including for example traditional fiberglass casts, according to embodiments of the present invention.

As shown in FIG. 7, the paddle 106 may include one or more slots 150 that extend through the paddle 106. Each slot 150 may be placed at the junction between two paddle sections or on any single paddle section. The paddle 106 also features a strut connector 152 and a spring attachment feature 154. In one embodiment, the strut connector 152 forms a wedge-shaped cavity 156 having an aperture 158 on one end of the wedge for receiving a strut 104. The spring attachment feature 154 may be a rectangular aperture formed by a lower edge 160 and surrounding edges 162, 164, and 166. The lower edge 160 is longer than the width of the hook element 338 and the thickness of the lower edge 160 is less that the span of the hook element 338, so that the hook element 338 can clip over or otherwise engage the lower edge 160. In other embodiments, the spring attachment feature 154 includes a bar to which the hook element 338 couples. In other embodiments, spring element 300 and the strut attachment feature 154 are coupled via rivets, bolts, adhesive, or other coupling mechanisms. The paddle 106 may be formed of plastic, metal, or any other stiff, supportive material. The paddle 106 may be made of a plastic molded to include the components discussed above, according to embodiments of the present invention.

Figure 9:
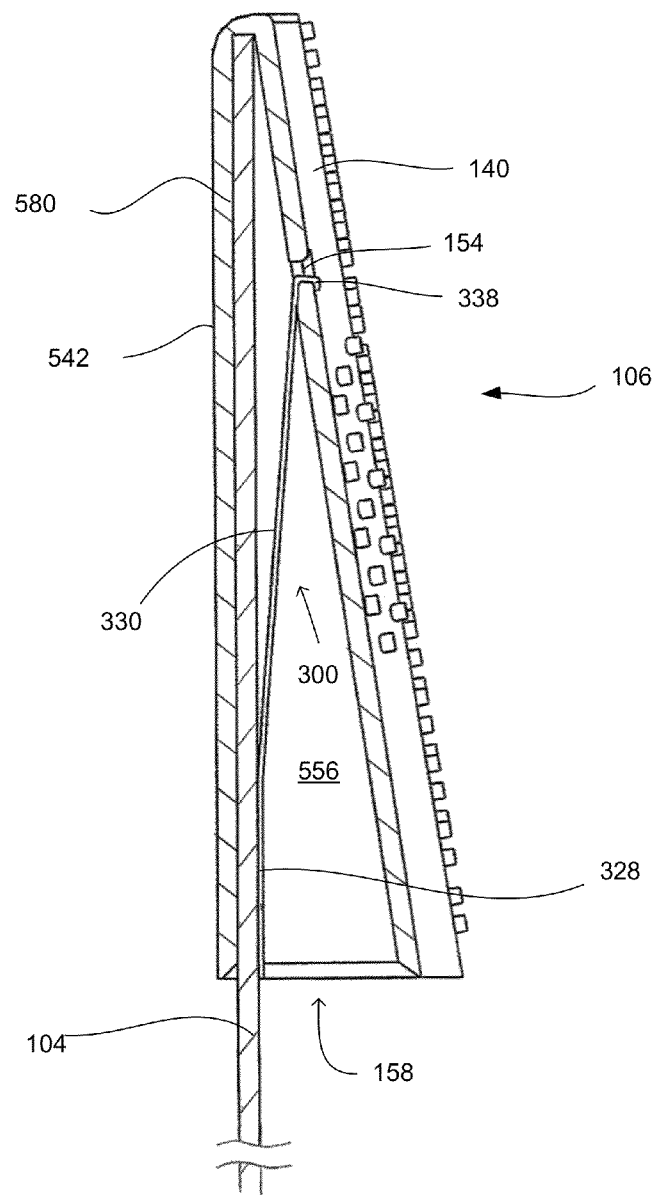
FIG. 9 illustrates a cut away side view of a paddle according to embodiments of the present invention.

FIG. 9 illustrates a cross section of paddle 106 and a side strut 104, according to embodiments of the present invention. The top end of the strut 104 extends into a wedge-shaped cavity 556 through aperture 158. The paddle 106 includes the inner surface 140 and an outer surface 542, according to embodiments of the present invention. The strut 104 may be coupled to the inside of the cavity 556; for example, the strut 104 may be riveted to or glued to the inside of the cavity 556 at interface 580, according to embodiments of the present invention. The spring element 300 is coupled to the strut 104 at strut attachment portion 328 (for example through apertures 334, 336), and the hook element 338 of the paddle attachment portion 330 hooks or clips onto the spring attachment features 154, according to embodiments of the present invention. The strut attachment portion 328 and paddle attachment portion 130 may each be substantially straight and flat sections formed integrally, with a bend or an angle at location 340 between the sections (see FIG. 7), according to embodiments of the present invention.

According to some embodiments of the present invention, an angle formed between the inner surface 140 and the outer side 580 (taken along the view of FIG. 9) changes to accommodate legs of different sizes and shapes. The spring element biases the inner surface 140 in a direction away from outer side 580 of the paddle 106, in a direction toward the user, according to embodiments of the present invention. This spring element 300 encourages the protrusions 148 to remain in contact with the patient's leg and/or an underlying orthotic device applied to the patient's leg, for example during ambulation. According to some embodiments of the present invention, the struts 104 themselves act as springs to bias the paddle 106 against the patient's leg or cast; this may be accomplished by, for example, forming or positioning the struts with a slight inward bend, such that the struts 104 are temporarily separated to accommodate the leg and then released to press snugly against the leg and/or underlying cast. In this way, the struts 104 act as leaf springs, according to embodiments of the present invention.

Figure 10:
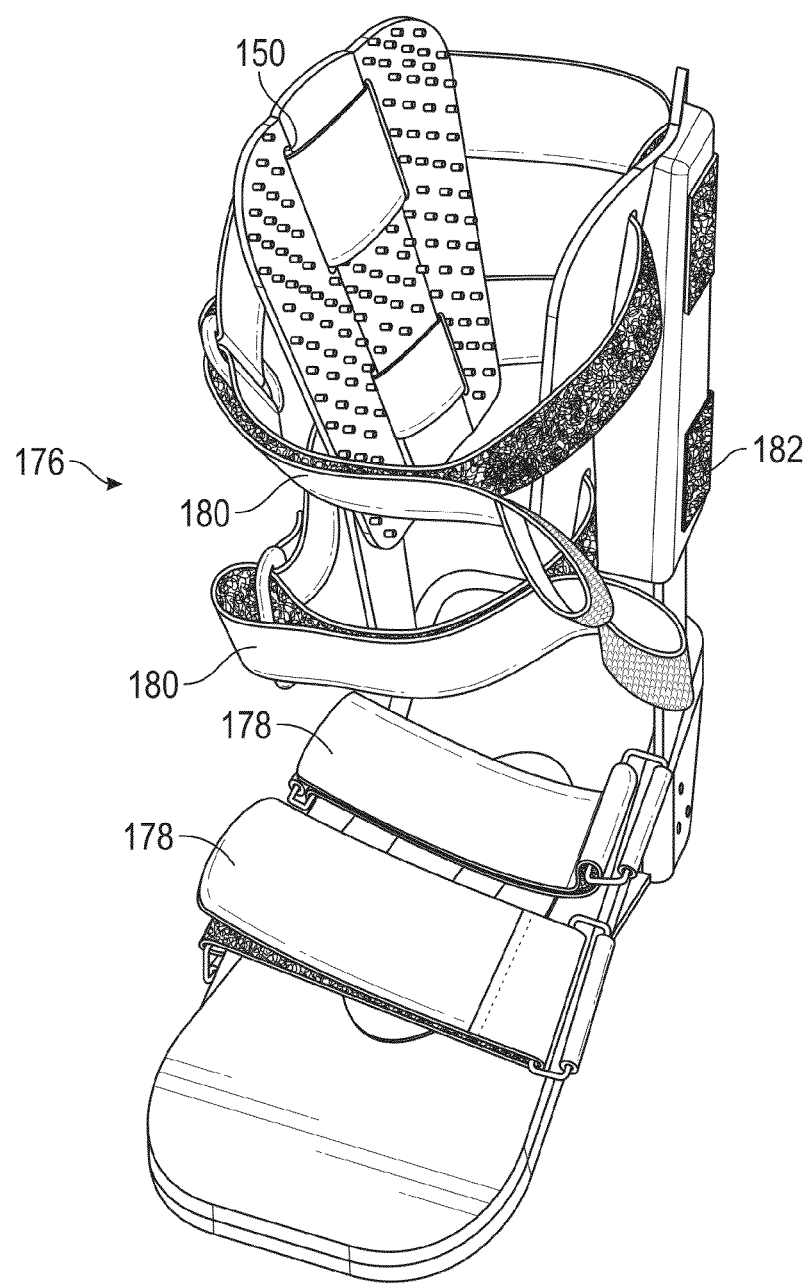
FIG. 10 illustrates a front perspective view of an off-weighting boot including a strap attachment system, according to embodiments of the present invention.

In one embodiment, the slots 150 in the paddle 106, as well as the rigid footbed 102 and/or sidewall portion 110, are configured to accommodate a strap coupling system 176, as shown in FIG. 10. In one embodiment, the strap coupling system 176 uses two footbed straps 178 and two paddle straps 180; other embodiments may employ only one footbed strap 178 and/or one paddle strap 180. Alternative embodiments may utilize more than two footbed straps 178, more than two paddle straps 180, or a combination of multiple footbed and multiple paddle straps. In one embodiment, the paddle straps 180 are formed of material having a hook section and loop section, and the straps are threaded through the paddle slots 150 so that the hook section couples to the loop section, as illustrated in FIG. 10. The footbed straps 178 are formed of similar material. The paddle 106 may also include patches 182 of loop material or hook material so that the paddle straps 180 can couple to the paddle 106 instead of, or in addition to, the straps themselves. The patches 182 may be secured to the paddle 106 through adhesive or other attachment mechanisms. The strap coupling system 176 may utilize other known mechanisms for securing the paddle straps 180 or footbed straps 178, such as, for example, male/female connectors, buckles, or locking mechanisms. The length of the footbed straps 178 and paddle straps 180 used in the strap coupling system 176 may be customized for each patient. The paddle straps 180 can also be a disposable strap configured to lock onto itself in a non-reversible way, such that it must be cut and replaced by a medical doctor or technician.

The strap coupling system 176 is one kind of circumferential cast attachment system. Other circumferential cast attachment systems may be used to hold the boot 100 against the cast 800. For example, a rubber band or other elastic band may be used to hold the struts 104 together around the cast 800 or the patient's leg. Another circumferential cast attachment system may include an elastic material that is wrapped around the struts 104 and the patient's leg and tied or clipped or otherwise tightened around the leg to hold the struts 104 against the cast 800 or the patient's leg, according to embodiments of the present invention. Another circumferential cast attachment system may include a clamp system which may be placed around the boot 100 and cast 800 in an open configuration, and clamped closed to secure the boot 100 against the cast 800. A clamp system may operate similarly to the clamp system of a ski boot, for example. Another circumferential cast attachment system may include a ratchet system which permits a circumferential device placed around the leg (e.g. a plastic or rubber strap) to be tightened and/or loosened incrementally. Another circumferential cast attachment system may include an outer boot or "clamshell"-type device which more fully encloses and/or covers the cast 800; such an outer boot may include an inner layer of foam or the like, such that when the outer boot is tightened about the cast 800, the inner layer of foam or the like conforms to the outer surface shape of the cast 800, thereby enhancing the mechanical engagement of the outer boot with the cast 800, according to embodiments of the present invention. Other circumferential cast attachment systems may include a combination of two or more circumferential cast systems, for example a combination clamp and ratchet system, according to embodiments of the present invention.

The two paddles 106 may be spread apart before placing the boot system 100 on the patient, and, once the boot is placed, the resiliency of the side struts 104 pushes the paddles 106 back into contact with the user's body or underlying orthopedic device, according to embodiments of the present invention. In addition, the resiliency of the side struts 104 can contribute additional securing forces by pushing the paddles 106 against the patient's body or orthopedic device. In one embodiment, the side struts 104 are formed of carbon graphite.

In some embodiments, footbed 102, the struts 104, and the paddles 106 are formed from thermoplastics, metal, rubber, or other similar materials. The support layers 116, 118, and 120 may be formed of an EVA-based material secured to the footbed 102 by pressure sensitive adhesive tape. Other embodiments use similar materials for the footbed 102, such as foams, silicones, polyurethanes, and the like.

Figure 11:
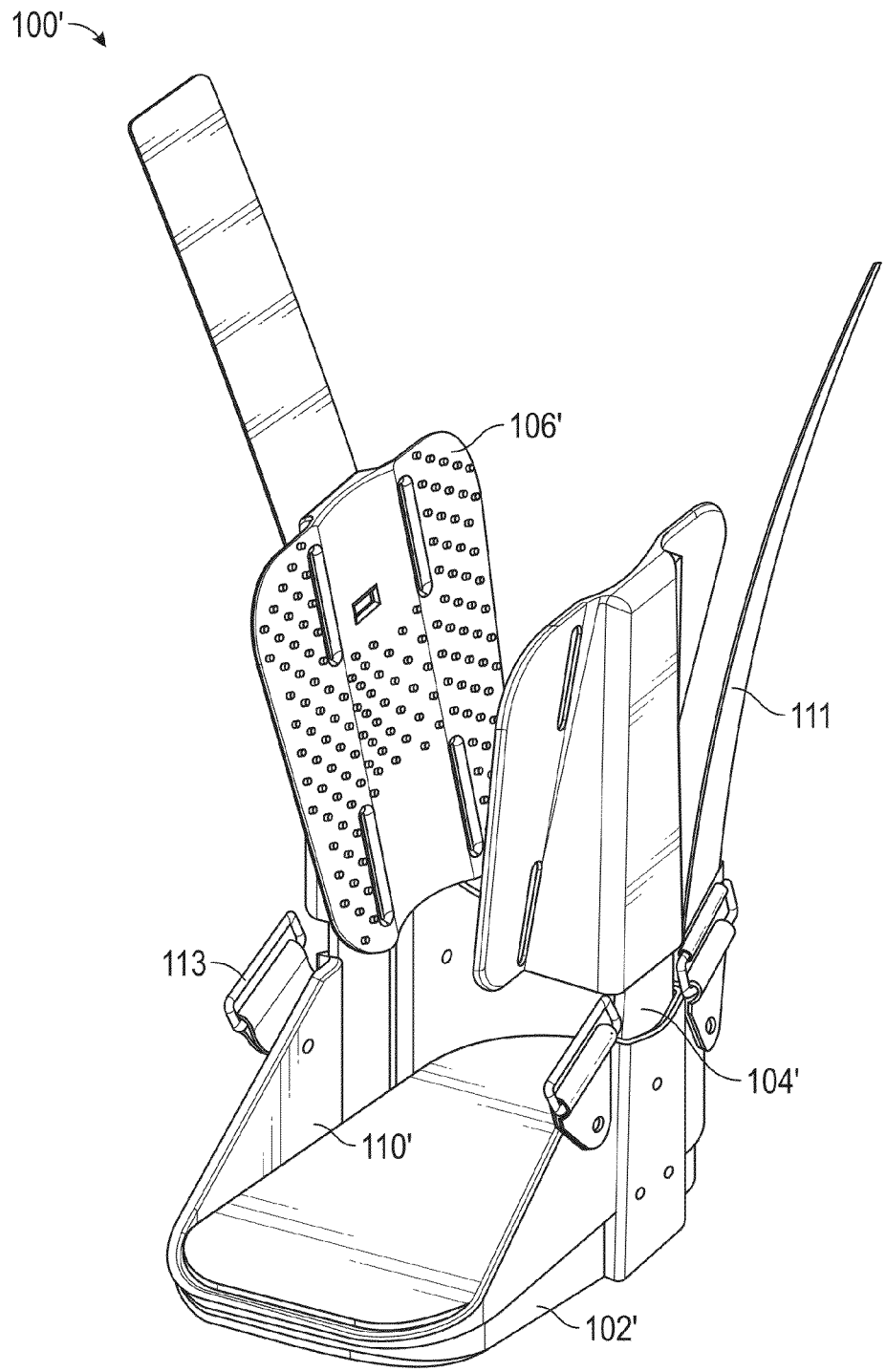
FIG. 11 illustrates a front perspective view of an alternative off-weighting boot that may be used for a patient who has undergone transmetatarsal amputation, according to embodiments of the present invention.
Figure 12:
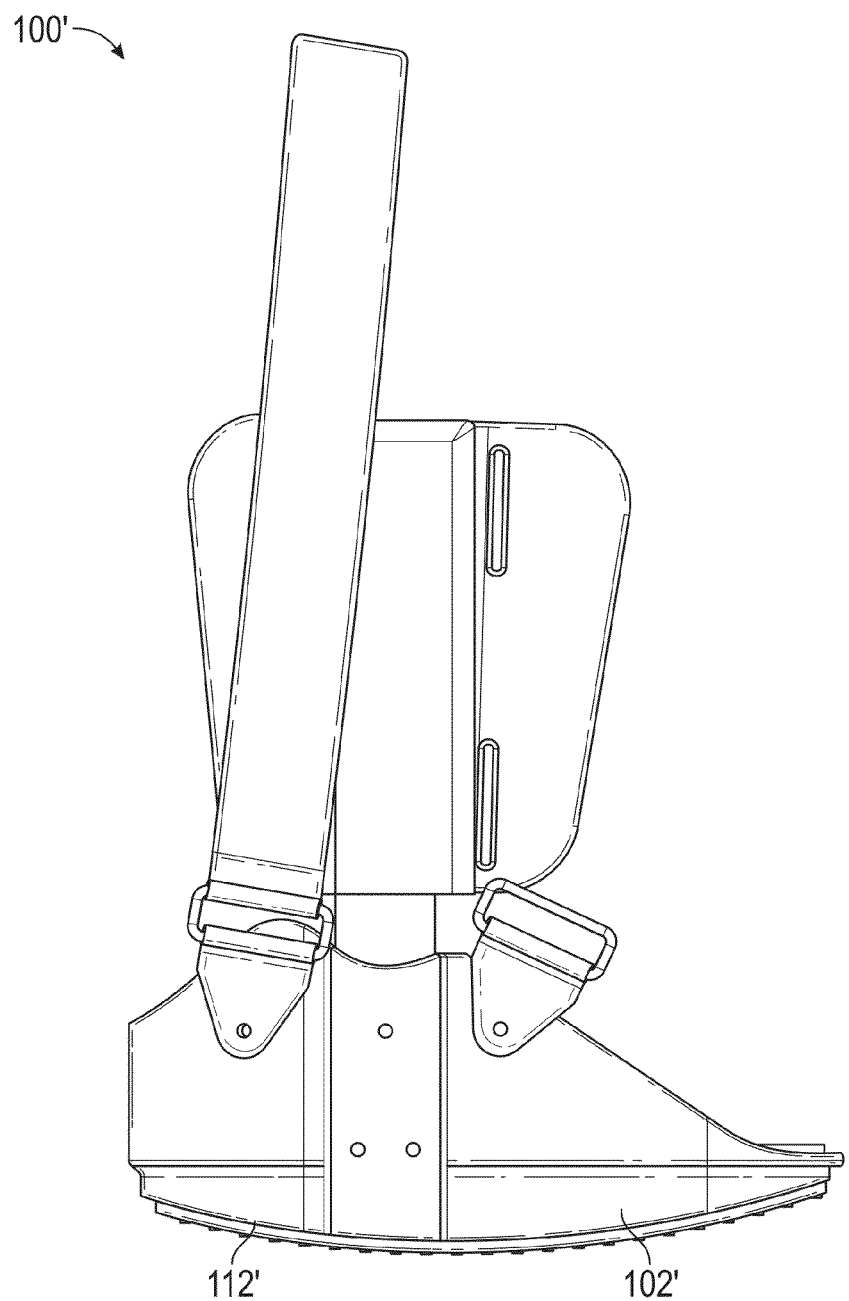
FIG. 12 illustrates a side elevation view of the off-weighting boot of FIG. 11, according to embodiments of the present invention.
Figure 13:
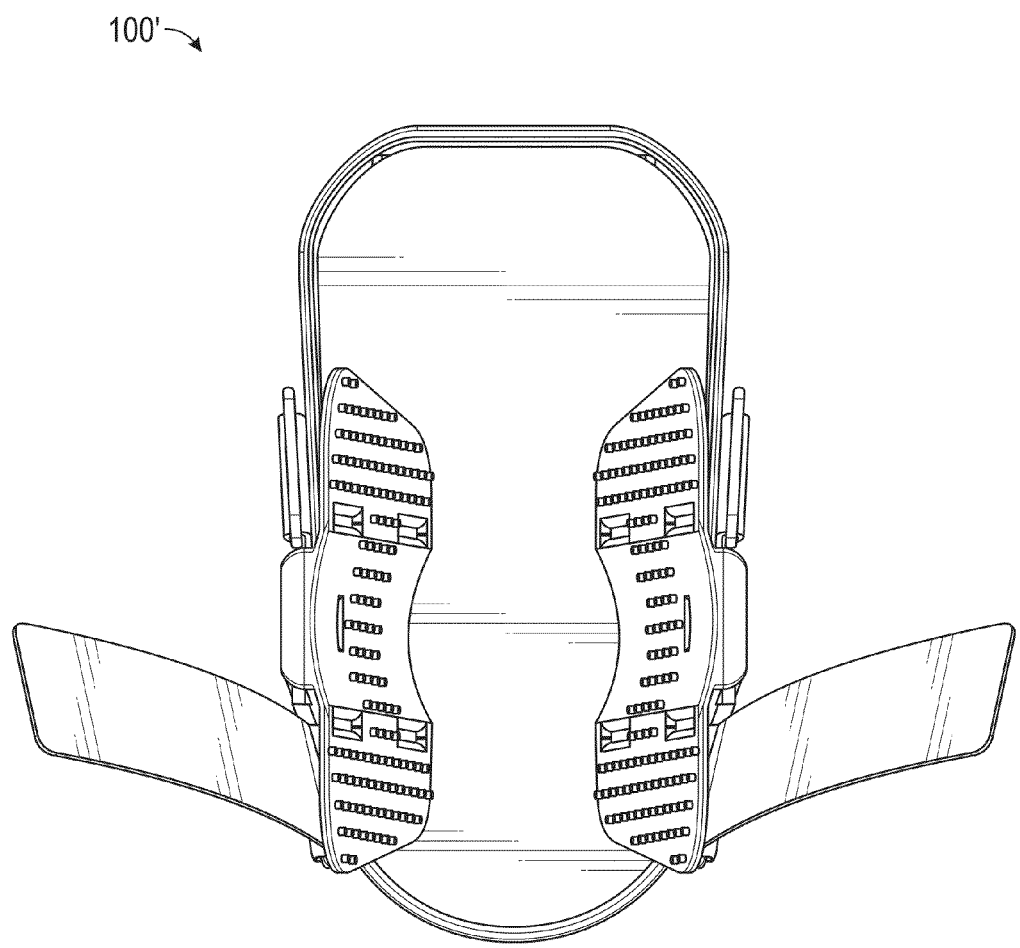
FIG. 13 illustrates a top plan view of the off-weighting boot of FIGS. 11 and 12, according to embodiments of the present invention.

FIGS. 11-13 illustrates an alternative off-weighting boot system 100' which is configured to be used with a patient who has undergone transmetatarsal amputation ("TMA"), according to embodiments of the present invention. In order to accommodate TMA patients, the footbed 102' of the boot system 100' is similar to footbed 102, but is shorter, according to embodiments of the present invention. Footbed 102' may also include a rocker sole 112', similar to rocker sole 112, according to embodiments of the present invention. Also, the struts 104' are shown as shorter than struts 104, although paddles 106' may be similar to or the same as paddles 106, according to embodiments of the present invention. The rigid sidewalls 110' of footbed 102' may be higher than sidewalls 110 so as to better retain the patient's foot within the boot system 100', according to embodiments of the present invention. Also, the boot 100' may include a slightly different strap system. For example, as shown in FIGS. 11-13, the boot 100' may include straps 111 extending from the back of each side of the footbed 102', and are configured to be criss-crossed over the patient's foot and secured to an attachment mechanism (e.g. a ring 113) on the opposite side of the footbed 102', according to embodiments of the present invention. This attachment system helps to deter the disengagement of the patient's foot and/or cast 800 from the boot system 100', according to embodiments of the present invention. Boots similar to boot 100 and/or 100' may also be used to secure an outer boot structure to a leg or a cast for other types of foot deformities, in addition to or instead of TMA, according to embodiments of the present invention.

The footbed 102' may receive a foot support assembly similar to or the same as foot support assembly 108, according to embodiments of the present invention. According to other embodiments of the present invention, the footbed 102' may instead, or may further, include a highly foamy or conformable material lining the bottom and/or sides 110' of the footbed 102', and configured to form to the contour's of the patient's foot. This conformance of the boot 100' material to the patient's foot may be particularly helpful for retaining the boot 100' on the foot or cast 800 of TMA patients, according to embodiments of the present invention. Also, the paddles 106' may function similarly to paddles 106 in that they further help to keep the boot 100' coupled to the cast 800 and/or the underlying limb, thereby providing a device 100' which is well-suited for use with TMA patients for a number of reasons.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An orthotic device, comprising:
   a footbed comprising an internal footbed and an external sole, wherein the internal footbed is substantially rigid;
   a first strut coupled to the footbed;
   a second strut coupled to the footbed;
   a paddle coupled to the first strut, the paddle comprising an inner surface configured to face a limb of a patient having a hard cast applied thereto;
   a first support layer located on the footbed, the first support layer comprising a first aperture; and
   a second support layer located on the first support layer, the second support layer comprising a second aperture larger than the first aperture and at least partially overlapping the first aperture,
   wherein the first support layer is denser than the second support layer.

2. The orthotic device of claim 1, further comprising:
   a third support layer located on the second support layer, the third support layer comprising a third aperture larger than the first and second apertures and at least partially overlapping the first and second apertures.

3. The orthotic device of claim 2, wherein the first support layer is adhered to the second support layer, and wherein the second support layer is adhered to the third support layer.

4. The orthotic device of claim 2, wherein the third support layer comprises perforations or markings for other apertures or differently sized apertures in addition to the third aperture.

5. The orthotic device of claim 1, wherein at least a portion of the second aperture is preformed in the second support layer.

6. The orthotic device of claim 5, wherein one or more other apertures are preformed in the second support layer.

7. The orthotic device of claim 1, further comprising:
   a foot support assembly located on the footbed, the foot support assembly molded as a single piece and comprising an aperture extending from a top to a bottom of the foot support assembly, wherein the aperture is configured to circumscribe a foot ulcer, a Charcot deformity, or a transmetatarsal amputation site, and wherein at least one dimension of the aperture decreases along a direction from the top to the bottom of the foot support assembly.

8. The orthotic device of claim 7, wherein the inner surface of the paddle comprises a mechanical interlock feature configured to minimize sliding of the paddle with respect to the hard cast applied to the limb and to increase an area over which forces from the first strut are transmitted to the hard cast.

9. The orthotic device of claim 2, wherein the second support layer is denser than the third support layer.

10. The orthotic device of claim 1, wherein the first support layer is adhered to the second support layer.

11. The orthotic device of claim 1, wherein the second aperture is at least partially enclosed by one or more of a mesh, a thinner layer, a material that is at a lower density than material out of which the second aperture is formed, and a memory foam.

12. The orthotic device of claim 1, wherein the second support layer comprises perforations or markings for other apertures or differently sized apertures in addition to the second aperture.

13. The orthotic device of claim 1, wherein the external sole is an external rocker sole configured to permit ambulation.

14. The orthotic device of claim 1, wherein the inner surface of the paddle comprises a mechanical interlock feature configured to minimize sliding of the paddle with respect to the hard cast applied to the limb and to increase an area over which forces from the first strut are transmitted to the hard cast.

* * * * *